(12) United States Patent
Glynn

(10) Patent No.: US 6,171,535 B1
(45) Date of Patent: Jan. 9, 2001

(54) PROCESS FOR THE MANUFACTURE OF ORTHOTIC JOINTS

(75) Inventor: Daniel W. Glynn, Pembroke, MA (US)

(73) Assignee: Glynn Orthopedics Services Inc, Pembroke, MA (US)

(*) Notice: Under 35 U.S.C. 154(b), the term of this patent shall be extended for 0 days.

(21) Appl. No.: 09/211,545

(22) Filed: Dec. 15, 1998

(51) Int. Cl.⁷ ..................................... B29D 7/00
(52) U.S. Cl. ..................... 264/159; 264/152; 264/258
(58) Field of Search ................................ 264/222, 159, 264/242, 152, 258

(56) References Cited

U.S. PATENT DOCUMENTS

| | | | |
|---|---|---|---|
| 5,573,501 | * 11/1996 | Ruscito et al. | 602/7 |
| 5,766,724 | * 6/1998 | Tailor et al. | 428/110 |
| 5,772,945 | * 6/1998 | Brown | 264/258 |
| 5,817,041 | * 10/1998 | Bader | 602/23 |

* cited by examiner

Primary Examiner—Jan H. Silbaugh
Assistant Examiner—Stefan Staicovici
(74) Attorney, Agent, or Firm—Hale and Dorr LLP

(57) ABSTRACT

The process for fabricating an orthotic joint of the present invention involves creating a casting mold of the anatomical joint for which the brace is being fitted. Then layers of nylon and cross-link carbon composite grade and the PVA bag are placed over the mold as is done in typical laminating processees for such braces. Then, a series of reinforcing strips of nylon and composite are attached to the layup in the same location where the sidebars would normally be located. The bottom layer which is typically a layer of nylon stockinette is the longest of the layers and the nylon strips are alternated with the composite strips with each successive strip being shorter than the strip immediately below it. A dummy disk is then provided at the joint. A second set of strips is then positioned where the upper sidebar would be located. Additional laminating substrate materials of nylon and cross-link carbon composite braid and a PVA bag are then placed over the structure. An acrylic/epoxy resin, accelerant and other materials used in the laminating process are poured over the brace. Once the layup is dried the brace is cut around the dummy disk partially through the brace from the outside on the lower-end and from the inside on the upper-end so that the brace can then be separated into two units. The dummy disk is then removed and a range of motion disk is inserted.

7 Claims, 3 Drawing Sheets

PROCESS FOR THE MANUFACTURE OF ORTHOTIC JOINTS

BACKGROUND OF THE INVENTION

The present invention is related to orthotic joints of rigid braces and more particularly to a manufacturing process for manufacturing orthotic joints which do not include sidebars.

Many different types of orthotic joints (such as knee joints) are currently in use. Almost every one of such joints have some mechanical joint made to flex and extend with the anatomical knee joints.

Typically, knee joints incorporated into long term knee ankle foot orthoses ("KAFO") (long leg brace) are made of steel with sidebars attached to thigh and calf cuffs. Individuals requiring long term braces generally obtain custom braces made from measurements and a casting of the affected limb. The braces are made by attaching sidebars to a steel joint that flexes and extends in the sagittal plane. A drop lock is pushed over the mechanical knee joint to lock the knee joint in place when the leg is fully extended so the knee will not buckle. Steel sidebars are, however, very heavy, and such weight limits the mobility of the brace wearer.

In U.S. Pat. No. 5,630,791 issued to Glynn, an orthotic joint is described which operates without the use of sidebars. In the joint described in the '791 patent a stop/locking lap joint is incorporated into a lap joint using a lamination. However, because separate steps are used with the calf sections (in the case of a knee joint) being laminated first and then laminating a thigh section over the calf section, the process for producing such a brace takes considerable time.

It is therefore a principal object of the present invention to provide a technique of fabricating an orthotic joint which does not utilize sidebars.

Another object of the present invention is to provide a method for producing an orthotic joint which is a laminated joint produced in a single laminating procedure.

Still another object of the present invention is to provide a method of producing a laminated orthotic joint without sidebars which does not display a significant decrease in rigidity when compared to joints with sidebars.

SUMMARY OF THE INVENTION

The process for fabricating an orthotic joint of the present invention involves creating a casting mold of the anatomical joint for which the brace is being fitted. Then layers of nylon and cross-link carbon composite grade and the PVA bag are placed over the mold as is done in typical laminating processees for such braces. Then, a series of reinforcing strips of nylon and composite are attached to the layup in the same location where the sidebars would normally be located. The bottom layer which is typically a layer of nylon stockinette is the longest of the layers and the nylon strips are alternated with the composite strips with each successive strip being shorter than the strip immediately below it. A dummy disk is then provided at the joint. A second set of strips is then positioned where the upper sidebar would be located. Additional laminating substrate materials of nylon and cross-link carbon composite braid and a PVA bag are then placed over the structure. An acrylic/epoxy resin, accelerant and other materials used in the laminating process are poured over the brace. Once the layup is dried the brace is cut around the dummy disk partially through the brace from the outside on the lower-end and from the inside on the upper-end so that the brace can then be separated into two units. The dummy disk is then removed and a range of motion disk is inserted.

These and other objects and features of present invention will be more fully understood from the following detailed description which should be read in light of the accompanying drawings in which corresponding reference numerals refer to corresponding parts throughout the several views.

DETAILED DESCRIPTION OF THE PREFERRED EMBODIMENTS

While the lamination technique described below will be described with respect to a knee orthotic joint, the principles will apply to other orthotic braces as well.

Figure 1:
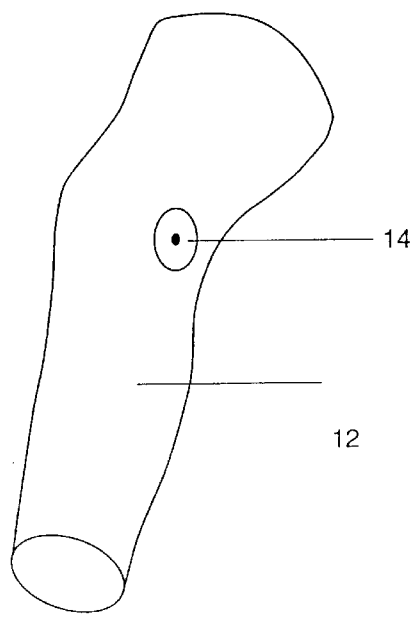
FIG. 1 is a perspective view of modified positive mold utilized in the process of present invention.
Figure 2:
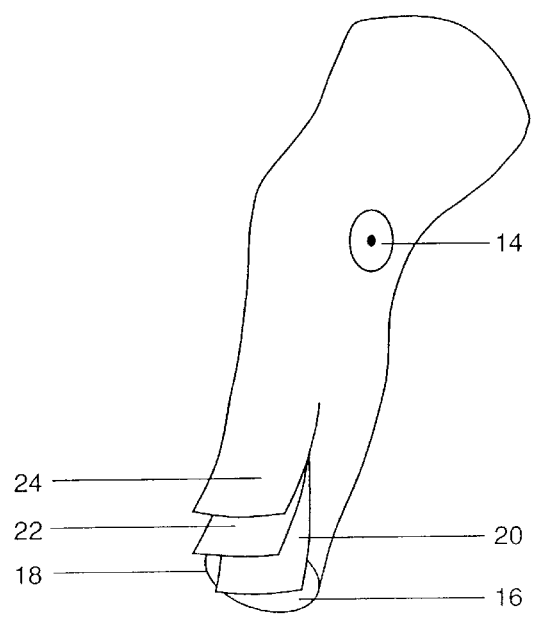
FIG. 2 is a perspective view of a mold of the type shown in FIG. 1 on which several layers of material used in the laminating process have been placed.
Figure 3:
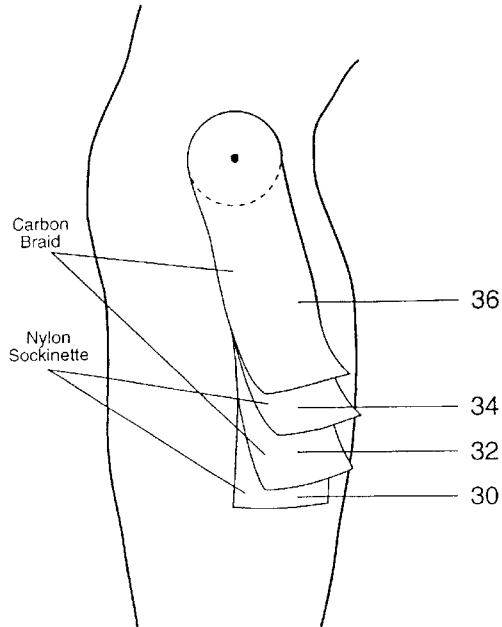
FIG. 3 is a perspective view of representative layers of reinforcement nylon and composite strips used in the process of the present invention.
Figure 4:
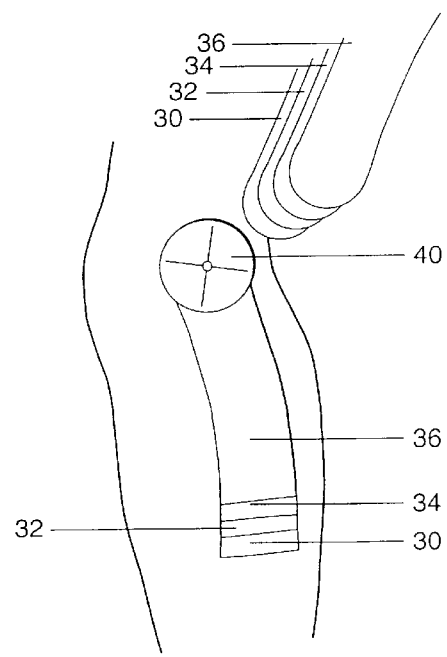
FIG. 4 is a perspective view of the repeated layering of a second reinforcement strip similar to the reinforcement strip shown in FIG. 3.

A positive mold 12 is formed out of plaster of paris, or substitute filler material used when CAD/CAM technology is used to turn digitized measurements into positive molds, for the knee for which the orthotic joint is made. A 2 inch diameter portion 14, which in a preferred embodiment is of a 3/16 inch depth, is cut out of the medial and lateral knee center borders of the mold 12. A 1/8 inch thick nylatron disk which in a preferred embodiment has a 2 inch diameter is plastered in place on both the medial and lateral sides of the knee center. As shown in FIG. 2 in which the materials are shown as being cut solely for illustrative purposes, a nylon stockinette and a polyethylene vinyl ("PVA") bag 18 placed in a wet towel (not shown) for 6 minutes is pulled tightly over the nylon stockinette 16 and the positive mold 12. Then two more nylon stockinettes 20, 22 are pulled over the layup. A layer 24 of cross-linked carbon composite braid, which in a preferred embodiment is 90° webbing, is glued and attached to the layup Referring now to FIG. 3, reinforcement nylon and composite strips are placed on the sides of the knee casting where the distal sidebars would be placed. In a preferred embodiment, a first 9 inch long by 2 inch wide strip of nylon stockinette 30, which is rounded at the top to fit the top of the arc of the diameter of the knee center 14, is attached to the knee center. Next, a carbon strip 32 which is slightly shorter than the nylon stockinette strip 30 is layered over the nylon stockinette strip 30. Then, the same procedure is repeated with a slightly shorter nylon stockinette strip 34 being placed over the carbon braid strip 32. Likewise, the carbon braid strip 36 which is placed over the nylon stockinette strip 34 is shorter than the nylon stockinette strip 34. The strips 30, 32, 34, 36 provide a layered reinforcement zone with the strongest reinforcement coming at and close to the knee.

An aluminum dummy separating disk 40 which in a preferred embodiment is ⅛ inch wide and 2½ inch in diameter is placed directly over the 2 inch diameter knee center. The steps described above of placing the alternating nylon stockinette and cross-linked carbon braid strips 30, 32, 34, 36 are then repeated for the thigh section of the joint.

Figure 5:
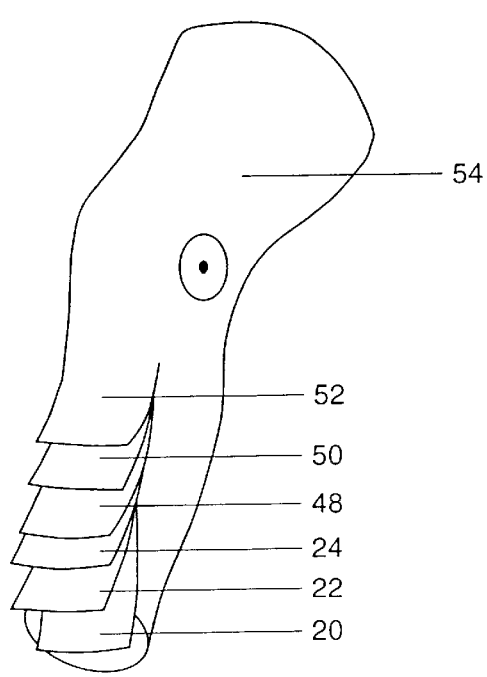
FIG. 5 is a perspective view of the mold shown in FIG. 4 on which several layers of composite materials have been layered before and after the reinforcing strips have been positioned.

Referring to FIG. 5, once the reinforcing strips are layered over the thigh section, a layer of cross-linked fiberglass braid 48, which in a preferred embodiment is a 45° angle webbing, is glued and attached to the layup. Then, two nylon stockinettes 50, 52 are placed over the layup before the final moistened PVA bag 54 is placed over the layup. While the invention has been described as including three layers under, and three layers over, the nylon stockinette strips, different numbers of layers can be used as long as the same number of layers of materials are applied under the nylon stockinette strips as over the strips. This ensures a uniform thickness for the brace. Then, as is the case with any lamination, an acrylic/epoxy resin is mixed with the paint pigment and accelerant and the mixture is poured in the top of the PVA bag and the resin is drawn down the leg hold until the materials are fully saturated.

Figure 6:
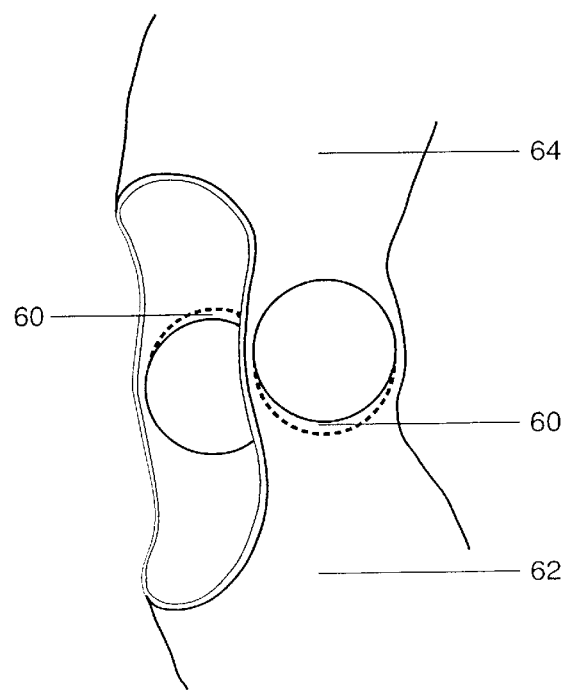
FIG. 6 is a perspective view of a laminate cut-off a cast which appears as one solid knee orthosis with no apparent knee joint.

Referring now to FIG. 6, the laminate is cut off the cast and appears as one solid knee orthosis with no apparent knee joint. The dummy disk is slightly larger than the replacement disks so that when the dummy disk is 2½ inches, the real replacement disks would be 2 inches in diameter. This ½ inch difference 60 is where the calf is to be cut out from the inside cutting outward in a radius of approximately ⅛ inch proximal to the knee center in a semicircle. Similarly, the thigh section is cut from the outside inward in a semicircle with an approximately 1⅛ radius distal to the knee. Both sets of cuts are done medially and laterally. These cuts allow the calf 62 and thigh 64 sections to be separated from each other. After separation the dummy disk 40 is removed from the calf section 62 to leave an overlapped thigh section 64 and underlapping calf section 62 at knee center. A nylatron disk 66, which in a preferred embodiment is a ⅛ inch thick and 2 inches in diameter 120° range of motion cut-out, is placed between the overlap and excess material removed as shown in FIG. 6. Such range of motion disks are described in U.S. Pat. No. 5,630,791, the teachings of which are incorporated herein by reference. The range of motion disk is aligned over the previously determined knee center on the underlapping calf extension 62 both medially and laterally.

The process of placing the nylatron disk 66 and creating a joint are described in U.S. Pat. No. 5,630,791, the teachings of which are incorporated herein by reference. In this process pre-drilled countersunk holes on the nylatron disk 66 are used as guides for drilling an attachment to the underlapping calf section extension 62. Dummy aluminum fillers (not shown) with drilled holes are placed in the range of motion cut-out slots. Holes are drilled through the dummy hole into the calf section 62 at the desired range of motion stop. The thigh section 64 is placed on top of the calf section 62 with the thigh extension 64 overlapping the nylatron disk 66 on the calf extension 62. A short bushing and screw is used at knee center to tighten the lap joint firmly.

Figure 7:
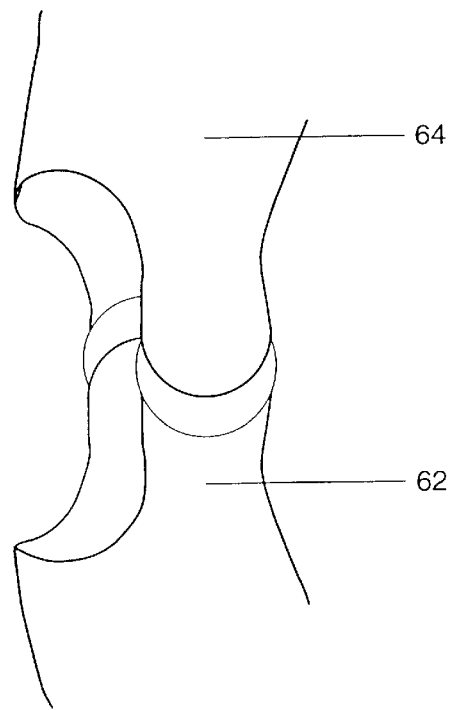
FIG. 7 is a perspective view of the orthotic joint manufactured according to the process of the present invention in which the thigh and calf pieces have been separated from each other.
Figure 8:
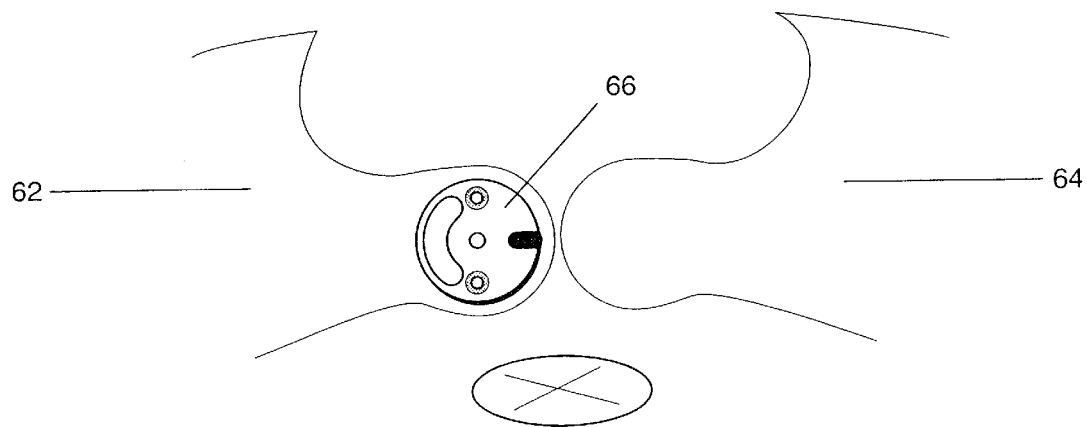
FIG. 8 is a plan view of the location of the insertion of a range of motion disk utilized in an orthotic joint manufactured according to the process of the present invention.
Figure 9:
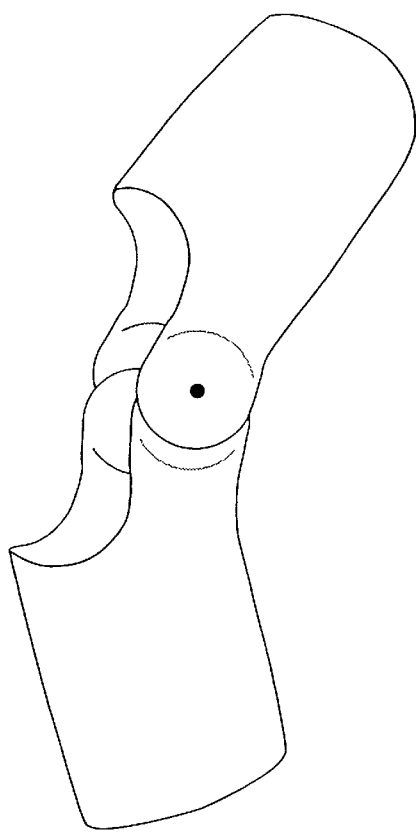
FIG. 9 is a perspective view of the completed orthotic joint manufactured according to the process of the present invention.

An extension stop is determined, as also described in U.S. Pat. No. 5,630,791, by extending the calf 62 and thigh 64 sections rotating on the bushing and screw to the desired position. A 90° drill pilots a hole from the inside of the calf extensions previous hole through the dummy hole and finally through the thigh overlap extension. The calf and thigh sections 62, 64 are then removed from each other. A clearance hole for a steel screw is drilled through the pilot hole on the thigh extension overlap. The dummy range of motion filler is removed and a desired stainless steel limiter is attached to the screw coming through the thigh extension. A short bushing and screw that we use only for tightening the lap joint together firmly for determining extension stop drilling are replaced with a longer steel bushing and screw equalling the diameter of the underlapped nylatron disk and overlap. The lap joint will move freely with the medial and lateral stainless steel limiters stopping the extension in unison as shown in FIG. 7.

The joint described above is made up of an acrylic/epoxy resin matrix material reinforced with oriented, continuous fibers of carbon and glass layered up in a multi-layer fashion. This type of layup forms a rigid and strong structure. This orthosis combines carbon fibers braided at 90° and a separate braid of 45° to get multi-dimensional reinforcement. It also adds a fiberglass braid near the outside of the shells. Fiberglass offers superior plasticity characteristics that are associated with bending flexure stresses. The outstanding design properties of carbon fiber resin matrix composites are their high strength to weight and stiffness to weight ratios. With proper selection of placement and fibers, the composites can be stronger and stiffer than equivalent thickness steel parts and weigh 40% to 70% less. Fatigue resistance of continuous fibers is excellent. Moreover, the resin utilized in the present invention is easy to use like a polyester material, but has the strength of acrylic. It is a chemically balanced mixture of the two types of acrylic/epoxy resin produced by Cascade Orthopedic Supply, Inc.

Materials such as fiberglass and kevlar can be substituted or added for increasing strength or flexibility depending on the characteristics that are required for individual customization of each client. One of the benefits of this technique of substituting composites for sidebars is that there are no toolings costs involved with changing the strength and/or size of the joint. Present metal sidebar joint systems do not make a large variety of molds for different sizes because it is cost prohibitive. The technique of making a lap joint in one lamination allows for an endless combination of material substrates to be used according to the strength, flexibility, and weight required during customization for each client. It is the technique and method of making a lap joint in one lamination that makes this system uniquely customizable at a lower cost While the foregoing invention has been described with reference to its preferred embodiments, various alterations and modifications will occur to those skilled in the art. All such alterations and modifications are intended to fall within the scopes of the appended claims.

What is claimed is:

1. A process for manufacturing an orthotic brace for supporting an anatomical joint without sidebars, said process comprising the steps of:

placing a first set of layers of laminate substrate materials over a casting of a body joint over which the orthotic brace is to be fit;

fixing a set of support strips including at least two nylon stockinette strips and at least two carbon strips arranged in alternating fashion in a lateral location on a side of said brace with a first end of each of said strips being attached at a joint center location of said brace intended to cover a center of said joint and extending in a first direction from said attachment location;

inserting a dummy disk over the joint center location, said dummy disk being placed over the portion of said set of support strips attached at the joint center location;

placing a second layer of laminate substrate materials over said strips; and pouring resin over said layers of laminate substrate materials to create laminate structure.

2. The process for manufacturing an orthotic brace of claim 1 further comprising the step of fixing a second set of support strips including at least two nylon stockinette strips and at least two carbon strips arranged in alternating fashion in a lateral location on a side of said brace with a first end of each of said strips being attached at said location of said brace intended to cover a center of said joint and extending in a second direction from said attachment location said second direction being different than said first direction.

3. The process for manufacturing an orthotic brace of claim 1 further comprising the step of fixing a second set of support strips including at least two nylon stockinette strips and at least two carbon strips arranged in alternating fashion in a lateral location on a side of said brace with a first end of each of said strips being attached over said dummy disk at said joint center location and extending in a second direction from said attachment location said second direction being different than said first direction.

4. The process for manufacturing an orthotic brace of claim 1 further comprising the steps of:

after said brace has hardened, making a partial cut through said brace through an inside surface of said brace, said cut being made along an edge of said dummy disk;

making a partial cut through said brace through an outside surface of said brace, said cut being made along an edge of said dummy disk;

separating said brace into two components at the location of said cuts and removing said dummy disk from said brace.

5. The process for manufacturing an orthotic brace of claim 1 wherein said layers of substrate support materials comprise at least one nylon stockinette and at least one layer of cross-linked carbon composite braid.

6. The process for manufacturing an orthotic brace of claim 1 wherein each support strip in said set of support strips is of a different length, said lengths being ordered when said strips are stacked in said set by length of said strip.

7. The process for manufacturing an orthotic brace of claim 5 wherein at least one layer of carbon composite is braided at 90° and at least a second layer of carbon composite is braided at 45°.

* * * * *